(12) United States Patent
Modglin

(10) Patent No.: US 7,025,737 B2
(45) Date of Patent: Apr. 11, 2006

(54) SPINAL BRACE HAVING OVERLAPPING RIGID MEMBERS

(75) Inventor: Michael D. Modglin, Braselton, GA (US)

(73) Assignee: DeRoyal Industries, Inc., Powell, TN (US)

( * ) Notice: Subject to any disclaimer, the term of this patent is extended or adjusted under 35 U.S.C. 154(b) by 0 days.

(21) Appl. No.: 10/738,796

(22) Filed: Dec. 17, 2003

(65) Prior Publication Data

US 2004/0133138 A1     Jul. 8, 2004

Related U.S. Application Data

(60) Provisional application No. 60/437,853, filed on Jan. 3, 2003.

(51) Int. Cl.
*A61F 5/00* (2006.01)

(52) U.S. Cl. .......................................... 602/19; 602/20

(58) Field of Classification Search .................. 602/19, 602/5, 32, 36, 9, 12; 128/96.1, 100.1, 102.1–106
See application file for complete search history.

(56) References Cited

U.S. PATENT DOCUMENTS

| | | | |
|---|---|---|---|
| 2,800,129 A | 7/1957 | Van Swaay | |
| 3,756,226 A | 9/1973 | Calabrese et al. | |
| 3,945,376 A | 3/1976 | Kuehnegger | |
| 3,957,040 A | 5/1976 | Calabrese | |
| 4,080,962 A * | 3/1978 | Berkeley | 602/19 |
| 4,178,923 A * | 12/1979 | Curlee | 602/13 |
| 4,285,336 A | 8/1981 | Oebser et al. | |
| 4,289,122 A | 9/1981 | Mason et al. | |
| 4,413,619 A | 11/1983 | Garth | |
| 4,475,543 A * | 10/1984 | Brooks et al. | 602/19 |
| 4,502,471 A | 3/1985 | Owens | |
| 4,508,110 A | 4/1985 | Modglin | |
| 4,515,153 A | 5/1985 | Calabrese | |
| 4,602,442 A | 7/1986 | Revill et al. | |
| RE32,219 E | 8/1986 | Garth | |
| 4,677,969 A | 7/1987 | Calabrese | |
| 4,778,717 A | 10/1988 | Fitchmun | |
| 4,886,052 A | 12/1989 | Calabrese | |
| 4,976,257 A * | 12/1990 | Akin et al. | 602/19 |
| D314,623 S | 2/1991 | Calabrese et al. | |
| 4,993,409 A * | 2/1991 | Grim | 602/19 |
| 5,012,798 A * | 5/1991 | Graf et al. | 602/19 |

(Continued)

FOREIGN PATENT DOCUMENTS

DE       42 11 077 A1    10/1993

(Continued)

OTHER PUBLICATIONS

The University of Iowa, Virtual Hospital: Pelvis & Perineum: Image: Iliac Crest 1992-2003 http://www.vh.org/adult/provider/radiology/pelvis/Lateral09.html.

*Primary Examiner*—Henry Bennett
*Assistant Examiner*—Shumaya B Ali
(74) *Attorney, Agent, or Firm*—Luedeka, Neely & Graham P.C.

(57) ABSTRACT

A spinal orthosis including a posterior support having a substantially rigid posterior splint, an anterior support having a substantially rigid anterior splint, and a pair of overlapping supports having substantially rigid splints are releasably attachable to the posterior support. The rigid splints of the overlapping supports overlap a portion of the posterior splint and the anterior splint when the orthosis is installed on a user.

5 Claims, 18 Drawing Sheets

U.S. PATENT DOCUMENTS

| | | | |
|---|---|---|---|
| 5,054,475 A | 10/1991 | Calabrese et al. | |
| 5,072,725 A | * 12/1991 | Miller | 602/19 |
| 5,097,824 A | 3/1992 | Garth | |
| 5,180,361 A | 1/1993 | Moore et al. | |
| 5,230,698 A | 7/1993 | Garth | |
| 5,344,391 A | 9/1994 | Modglin | |
| 5,437,612 A | 8/1995 | Moore et al. | |
| 5,474,523 A | 12/1995 | Miller | |
| 5,503,621 A | 4/1996 | Miller | |
| 5,573,501 A | 11/1996 | Ruscito et al. | |
| 5,620,412 A | 4/1997 | Modglin | |
| 5,622,529 A | 4/1997 | Calabrese | |
| 5,632,722 A | 5/1997 | Tweardy et al. | |
| 5,688,229 A | * 11/1997 | Bauer | 602/18 |
| 5,765,224 A | * 6/1998 | Johnson | 2/44 |
| 5,797,713 A | 8/1998 | Tweardy et al. | |
| 5,833,638 A | * 11/1998 | Nelson | 602/19 |
| 5,853,378 A | 12/1998 | Modglin | |
| 5,911,697 A | * 6/1999 | Biedermann et al. | 602/19 |
| 5,967,998 A | * 10/1999 | Modglin | 602/19 |
| 6,067,665 A | * 5/2000 | DePalma et al. | 2/468 |
| 6,071,255 A | 6/2000 | Calabrese | |
| 6,102,879 A | * 8/2000 | Christensen et al. | 602/19 |
| 6,146,349 A | 11/2000 | Rothschild et al. | |
| 6,213,968 B1 | * 4/2001 | Heinz et al. | 602/19 |
| 6,254,560 B1 | 7/2001 | Tweardy et al. | |
| 6,267,741 B1 | * 7/2001 | Lerman | 602/18 |
| 6,270,469 B1 | 8/2001 | Mott | |
| 6,315,746 B1 | 11/2001 | Garth et al. | |
| 6,478,759 B1 | * 11/2002 | Modglin et al. | 602/19 |
| 6,503,217 B1 | 1/2003 | Gibbs et al. | |
| 6,666,838 B1 | * 12/2003 | Modglin et al. | 602/19 |
| 6,676,617 B1 | 1/2004 | Miller | |
| 6,776,767 B1 | * 8/2004 | Reinecke et al. | 602/19 |
| 2003/0073942 A1 | 4/2003 | Gibbs et al. | |

FOREIGN PATENT DOCUMENTS

| | | |
|---|---|---|
| EP | 0 253 335 B1 | 1/1988 |
| WO | WO 01/37764 A1 | 5/2001 |
| WO | WO 02/00147 A1 | 1/2002 |

\* cited by examiner

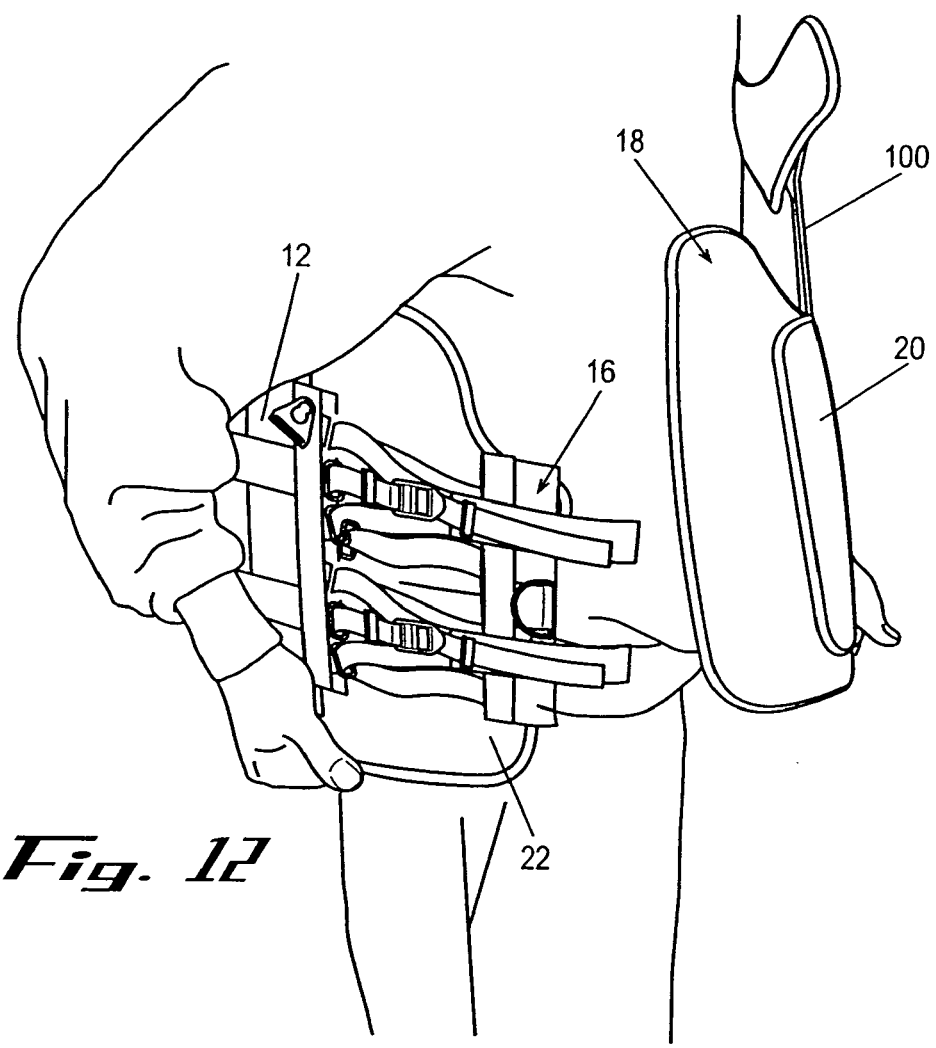
_Fig. 12_
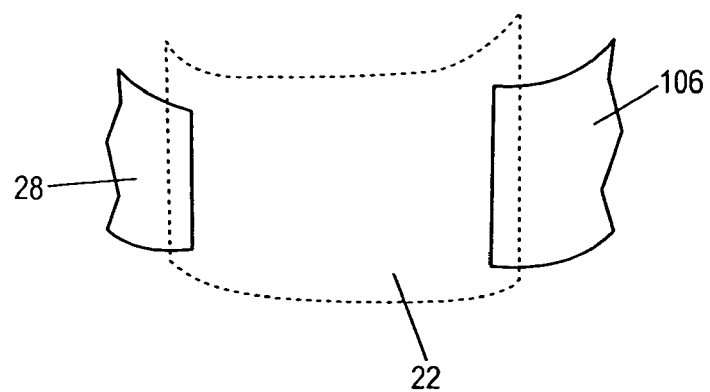
_Fig. 13_

US 7,025,737 B2

SPINAL BRACE HAVING OVERLAPPING RIGID MEMBERS

CROSS-REFERENCE TO RELATED APPLICATION

This is a continuation-in-part of provisional patent application Ser. No. 60/437,853, filed Jan. 3, 2003, and entitled "Spinal Brace Having Overlapping Rigid Members."

FIELD OF THE INVENTION

This invention relates generally to medical orthoses. More particularly, this invention relates to spinal braces having flexible materials incorporating rigid supports.

BACKGROUND AND SUMMARY OF THE INVENTION

Improvement is desired in the field of spinal braces and, in particular, spinal braces of the type having flexible materials incorporating rigid supports.

In a preferred embodiment, the invention relates to an improved spinal orthosis. The orthosis includes a posterior support having a substantially rigid posterior splint, an anterior support having a substantially rigid anterior splint, and a pair of overlapping supports having substantially rigid splints are releasably attachable to the posterior support. The rigid splints of the overlapping supports overlap a portion of the posterior splint and the anterior splint when the orthosis is installed on a user.

In a preferred embodiment, the overlap supports are each provided by a laminate made of a flexible foam material, a rigid plastic strip, and a rigid plastic sheet material sandwiched between a pair of soft flexible sheet materials to yield a substantially rigid laminate material shaped to substantially conform to a side portion of a patient.

In another embodiment, the overlapping supports are each provided by a flexible body defining a pocket and a substantially rigid, preferably polymeric, shell received within the pocket and configured to substantially conform to a side portion of a patient.

In yet another aspect, the overlapping supports are each provided by a flexible body having an internal stay of a substantially rigid material, the stay being generally conformable during installation of the orthosis on a user so as to be able to substantially conform to the shape of the user. The internal stay is preferably made of a sheet of polyethylene material having a base portion and a bifurcated portion defining a plurality of fingers.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

FIG. 12 shows installation of the brace of FIG. 1 onto a user.

FIG. 13 is a right side view showing the relationship between an overlap support and the posterior and anterior supports.

DETAILED DESCRIPTION

FIGS. 1–13.

Figure 1:
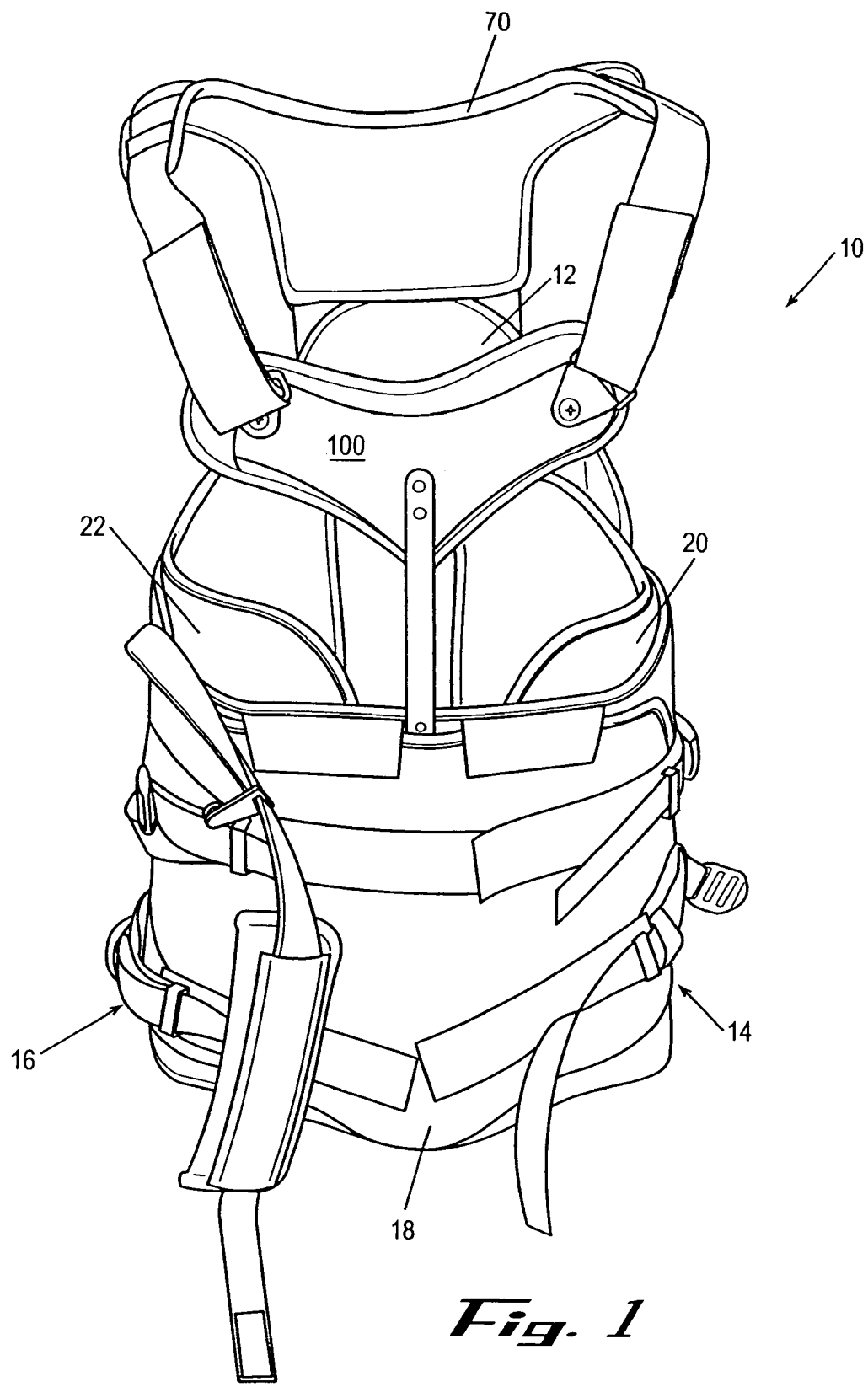
FIG. 1 is a front perspective view of a spinal brace in accordance with a preferred embodiment of the invention.

With initial reference to FIG. 1, the invention relates to a spinal brace 10 particularly configured to serve as a thoracic-lumbar-sacral orthosis (TLSO). The brace 10 includes as major components a posterior support 12, strap assemblies 14 and 16, anterior support 18, and overlap supports 20 and 22. The brace 10 is preferably positioned on a patient while supine.

It will be understood that the brace 10 may be otherwise configured for providing an orthosis suitable for treating other portions of the spine, such as the cervical portions. The brace 10 may also be configured to impart a particular orientation, such as a flexion, extension, or a neutral orientation to the spine.

Figure 2:
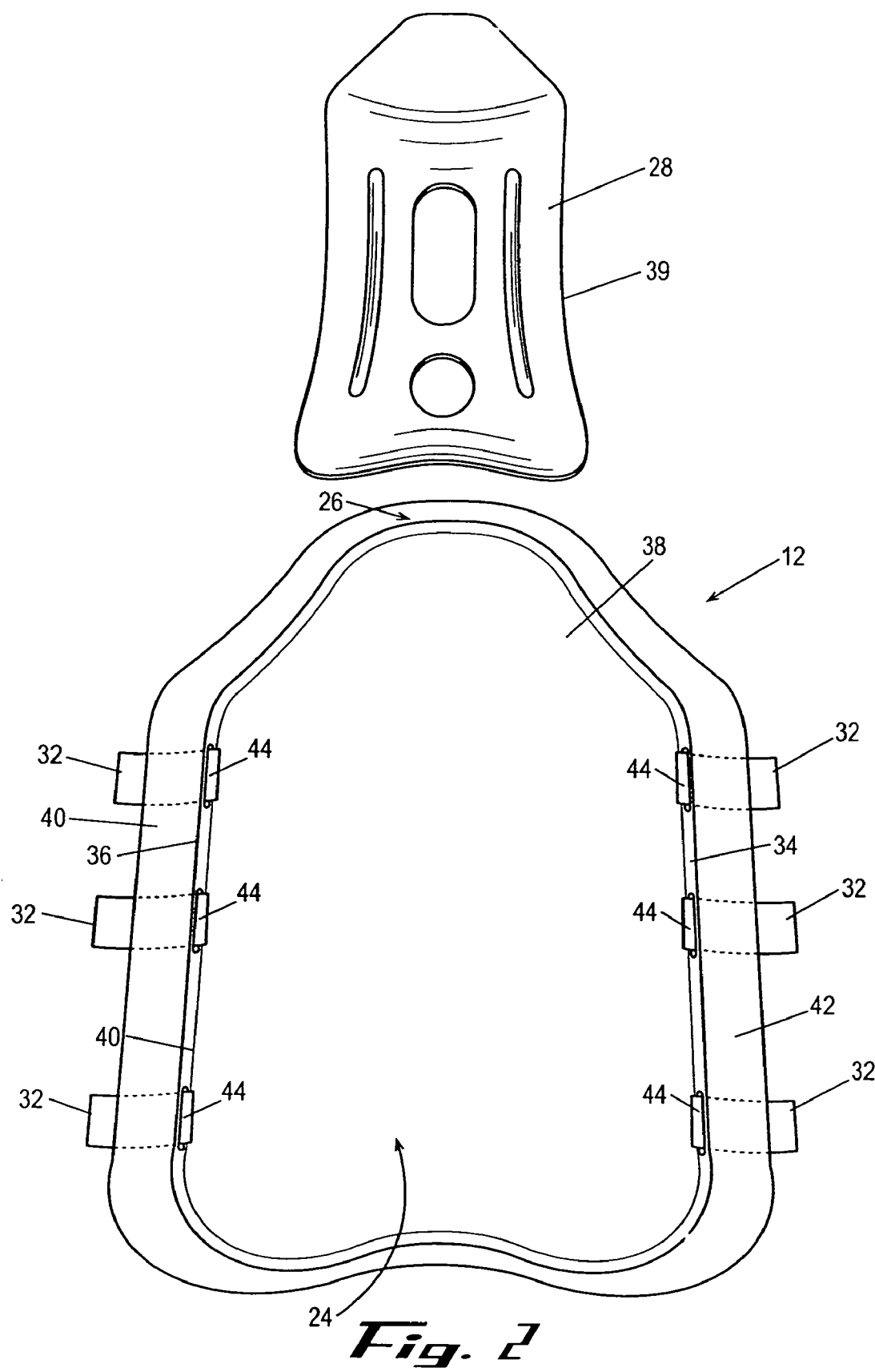
FIG. 2 shows a posterior support of the brace of FIG. 1.

With reference to FIG. 2, the posterior support 12 includes a foam body 24 having a pocket 26 for receiving a rigid splint 28. The body 24 is preferably formed of a soft breathable material laminated to a foam and having an outer surface 30 (FIG. 4) provided by a flexible loop material suitable for releasably engaging a flexible hook material.

A plurality of strips 32 of hook material extend from opposite side edges 34 and 36 of the body 24, adjacent to inner surface 38 of the body 24. The side edges 34 and 36 are preferably adjacent the periphery 39 of the splint 28 when it is installed within the body 24. The body 24 also preferably includes opposite side extensions 40 and 42 which extend from the side edges 34 and 36. The extensions 40 and 42 are preferably made of the same material as the body 24 and include internal rigid stays 43 (FIG. 6) running substantially the length of the extensions 40 and 42. The extensions 40 and 42 of the body 24 extend substantially beyond the portion of the body 24 that encases the rigid splint 28.

A plurality of slits 44 are preferably formed at the junctures between the side extensions 40 and 42 and their respective side edges 34 and 36 adjacent each of the strips 32. The strips 32 are preferably used to secure the overlap supports 20 and 22. However, in an optional configuration wherein one or more of the supports 20 or 22 are not used, the slits 44 permit the strips 32 to be positioned therethrough so as to extend around the exterior of the side extensions 40 and 42 and engage the anterior support 18.

The strap assemblies 14 and 16 may preferably correspond to the set of connection straps 300 or the lacings 820 and related assembly described in U.S. Pat. No. 6,478,759, issued Nov. 12, 2002, and entitled THORACO-LUMBROSACRAL ORTHOSIS, incorporated herein by reference in its entirety. The strap assemblies 14 and 16 may also preferably correspond to the latching assemblies 27 and 28 described in U.S. Pat. No. 5,967,998, issued Oct. 19, 1999, and U.S. Pat. No. 5,853,378, both entitled LUMBROSACRAL ORTHOSIS and incorporated herein by reference in their entirety.

Figure 3:
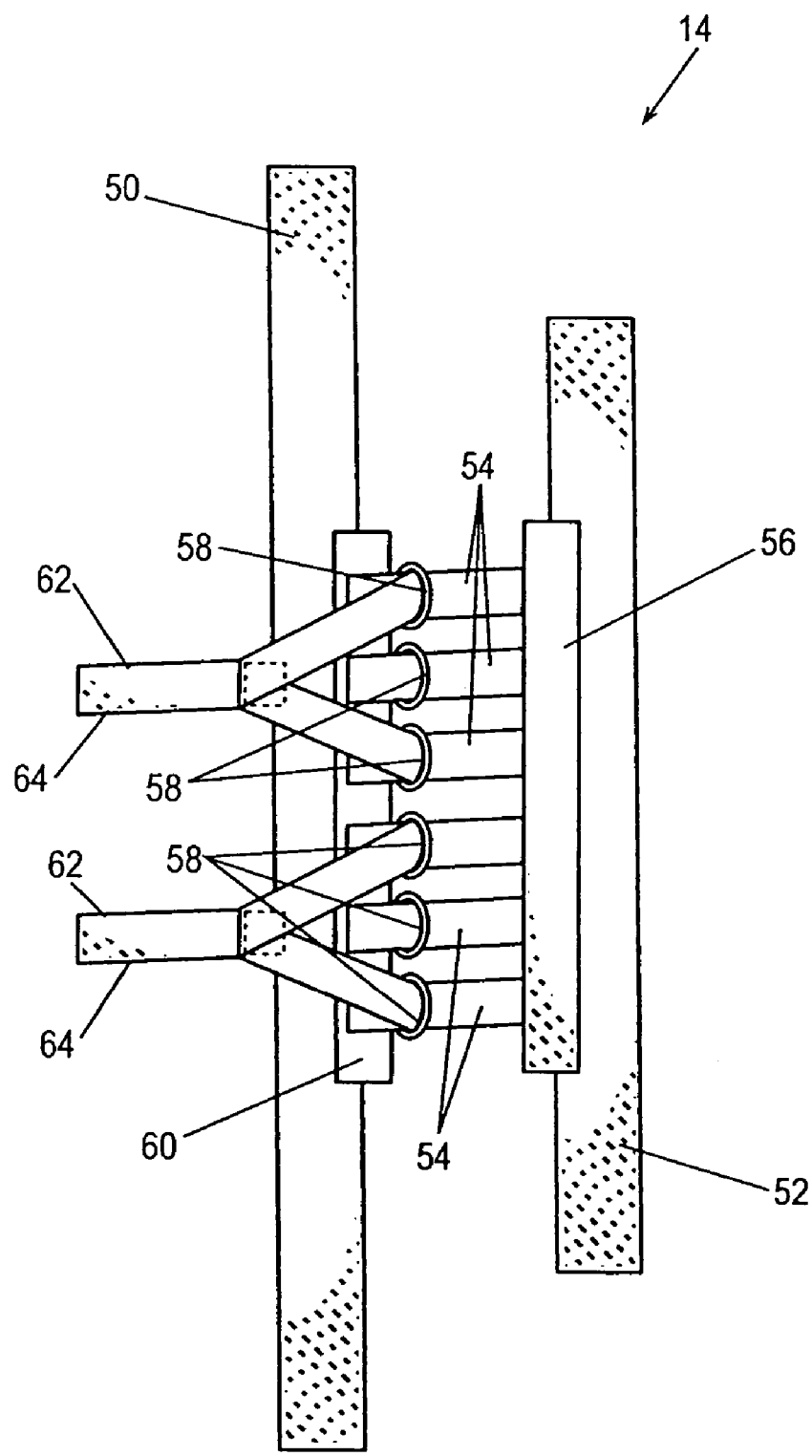
FIG. 3 shows a strap assembly of the brace of FIG. 1.
Figure 4:
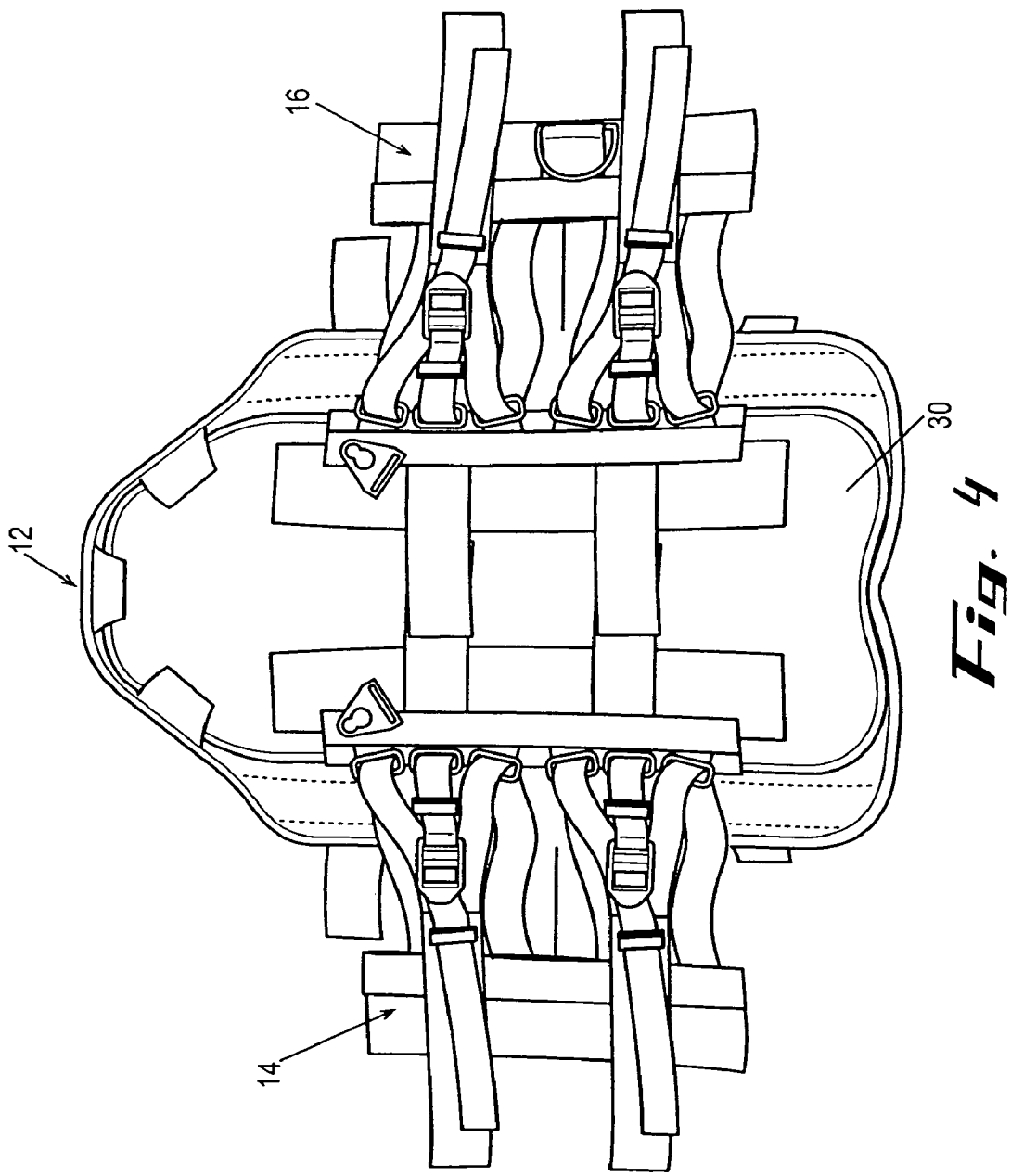
FIG. 4 shows the posterior support having a pair of strap assemblies installed thereon.

In this regard, and with reference to FIG. 3, the strap assembly 14 preferably includes a first crosspiece 50 and a second crosspiece 52, both formed of a hook and loop material such as is available under the trade name VELCRO. A plurality of straps 54 are attached to the second crosspiece 52 by a strip 56, preferably a nylon strip material. Each strap 54 extends through a loop 58, with each loop 58 attached to a strip 60, preferably a nylon strip. Groupings of the straps 54, preferably groupings of three, are attached to pull straps 62. The pull straps 62 preferably have a hook material 64 on the interior surface thereof so as to be positionable in releasable engagement with the anterior support 18. The strap assembly 16 is preferably identical to the strap assembly 14. As seen in FIG. 4, the strap assemblies 14 and 16 are installed on the posterior support 12 as by placing the hook material of the crosspieces 50 and 52 in contact with the loop material of the surface 30 of the posterior support 12. The strap assemblies 14 and 16 enable improved fit and provide lateral strength to the installed brace 10.

Figure 5:
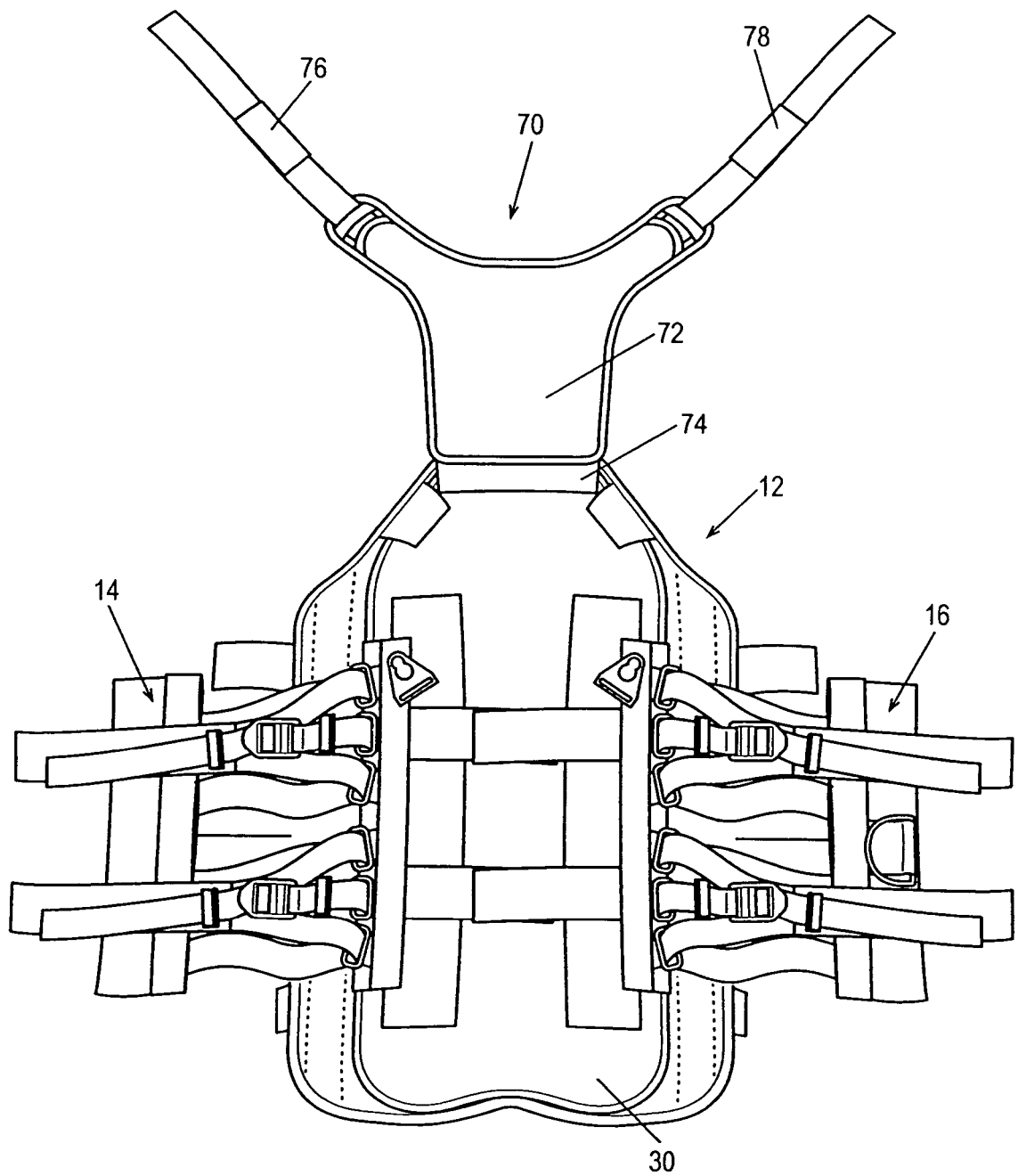
FIG. 5 shows the posterior support having a thoracic support installed thereon.

With reference to FIG. 5, a thoracic extension or support 70 is preferably installed on the posterior support 12 to provide additional bracing for the upper back/thoracic area. The thoracic support 70 preferably includes a generally Y-shaped padded body 72, a bottom flap 74, and flexible straps 76 and 78. The body 72 may include an interior pocket or cavity for receiving a rigid splint. In this regard, the thoracic support 70 preferably substantially corresponds to the thoracic support 700 described in U.S. Pat. No. 6,478,759, issued Nov. 12, 2002, and entitled THORACO-LUMBRO-SACRAL ORTHOSIS, incorporated herein by reference in its entirety.

Figure 6:
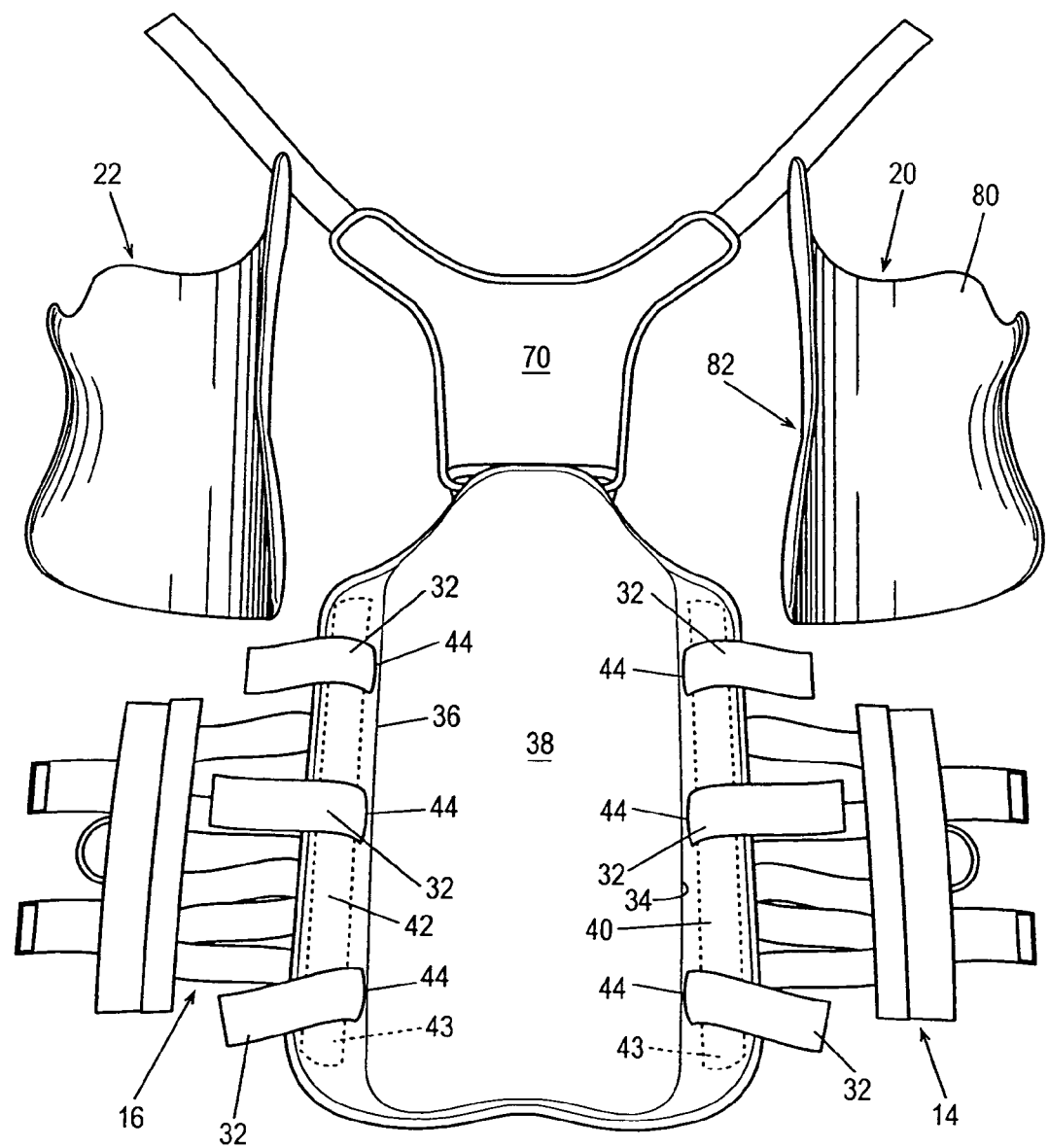
FIGS. 6–7 show overlap supports and their installation.
Figure 7:
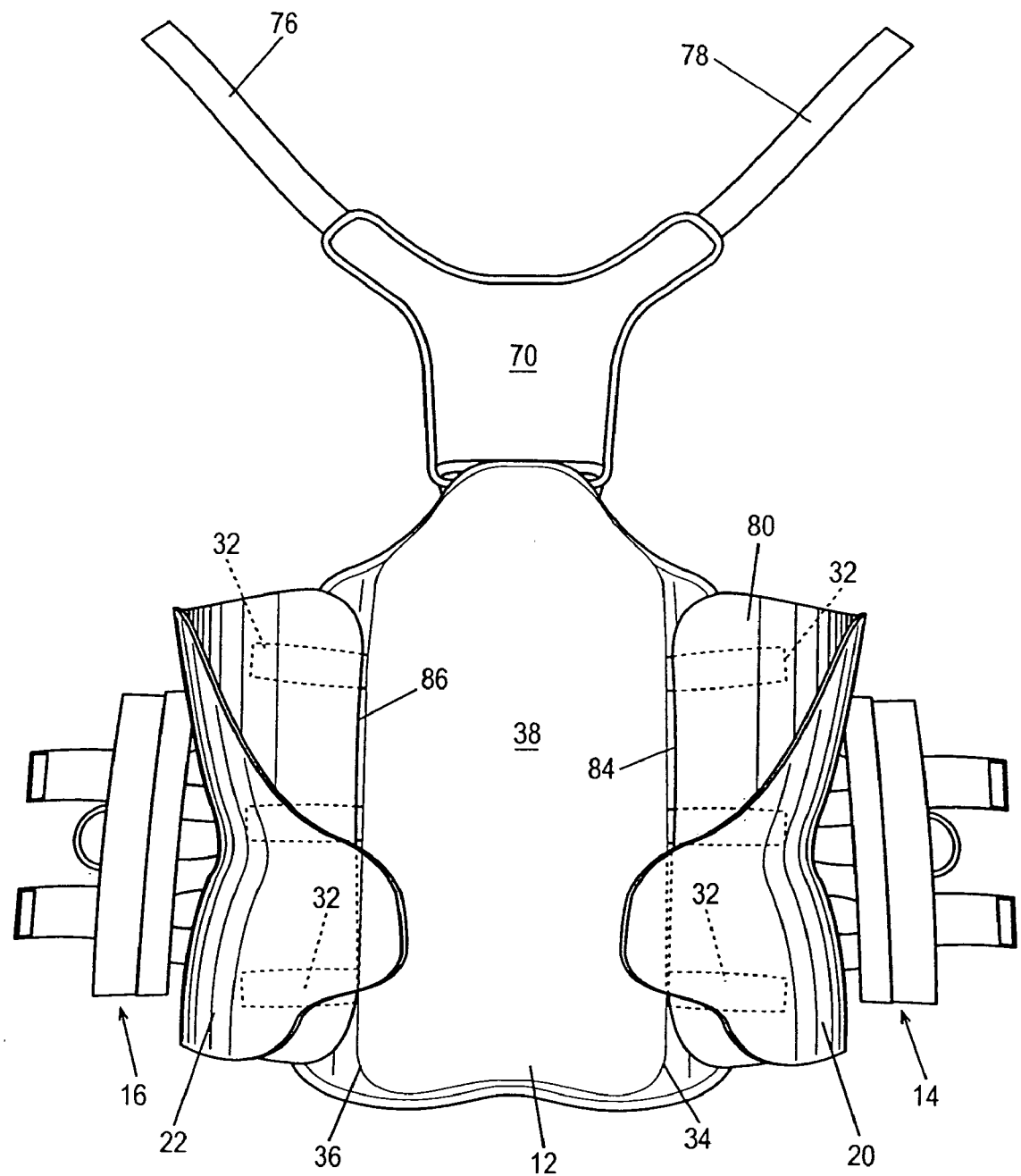

With reference to FIGS. 6–7, each overlap support 20 and 22 is preferably substantially rigid and curved or otherwise anatomically shaped to conform to the general curve of a patient's side, or, as describe below, may be custom fit to the patient. The support 20 preferably includes an interior or patient engaging surface 80 and an exterior surface 82, each made of a soft material that is capable of engaging hook material in the context of mating hook and loop materials, such as VELCRO. The support 22 is a mirror-image of the support 20 and includes interior and exterior surfaces 80 and 82 made of a hook engaging material. The exterior surfaces 80 of the supports 20 and 22 are engageable by the hook material of the strips 32 for installation of the supports 20 and 22 on posterior support 12 as seen in FIG. 7.

The supports 20 and 22 are preferably installed on the posterior support 12 with posterior edges 84 and 86 (FIG. 7) of the supports 20 and 22, respectively, overlapping the edges 34 and 36 of the support 12, so that the supports 20 and 22, which are themselves rigid, overlap at least a portion of the rigid splint 28 within the support 12.

Figure 8:
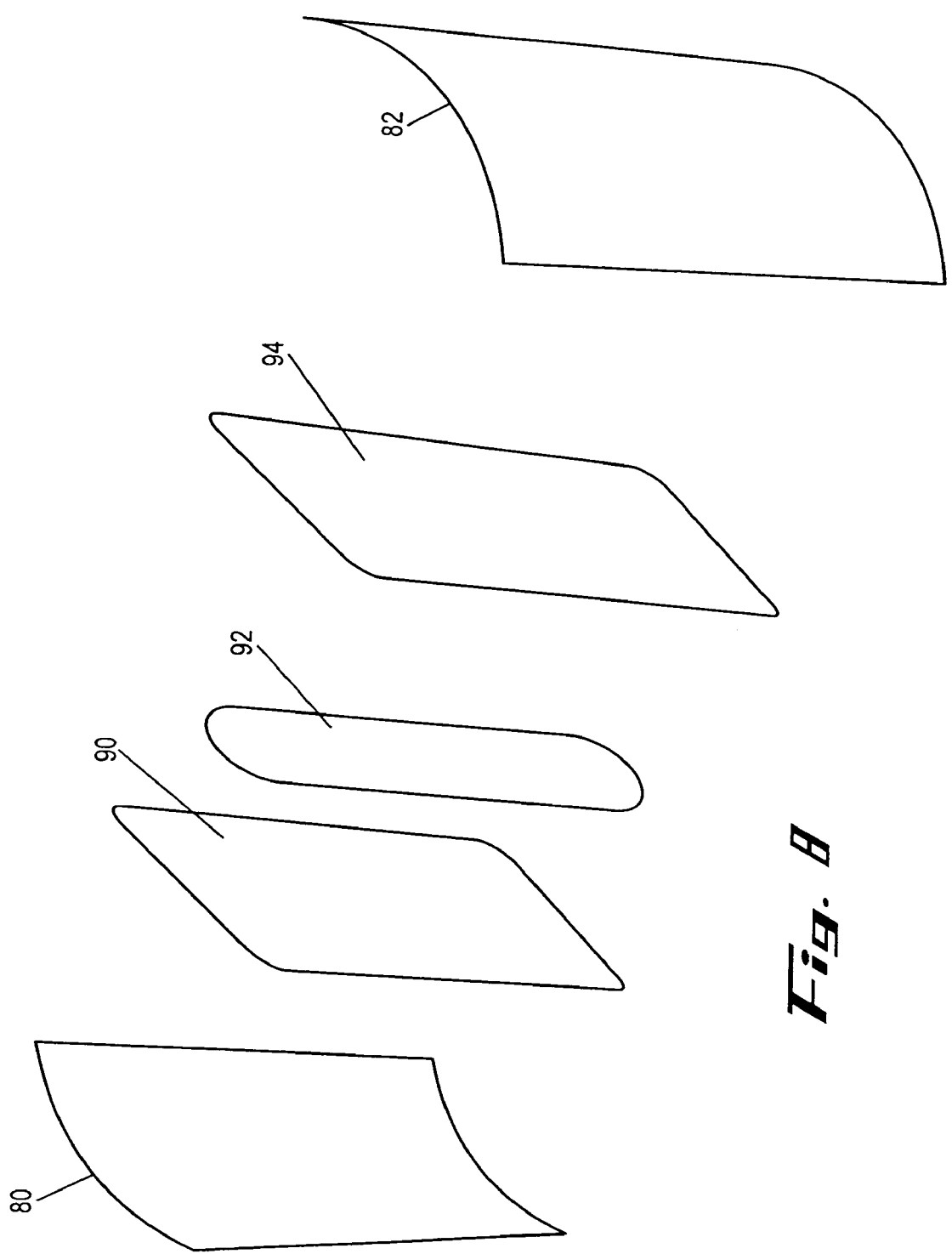
FIG. 8 is an exploded view of one of the overlap supports.

The supports 20 and 22 are each preferably of lightweight laminate construction. In this regard, and with reference to FIG. 8, sandwiched between the surfaces 80 and 82 is foam material 90, rigid plastic strip 92, and plastic sheet 94. The foam material 90 is preferably a sheet of about ⅛ inch thick closed cell foam material. The strip 92 is preferably a strip of about 1/16 inch thick ABS plastic. In the case of the support 20 having an overall width of about 12 inches, the width of the strip 92 is preferably about 3 inches, with its width beginning about 4 inches from the posterior edge 84. The sheet 94 is preferably a sheet of about 1/16 inch thick low density polyethylene. The supports 20 and 22 are preferably made as by vacuum molding with adhesive placed between each layer. The supports 20 and 22 may be heated if desired, as by a heat gun or oven, to soften them so that they may be custom fit to the patient. In configuring or custom-fitting the supports 20 and 22, it is desired that the supports 20 and 22 be shaped so as to wrap around the iliac crests of the patient and over the anterior superior iliac spines of the patient.

Figure 9:
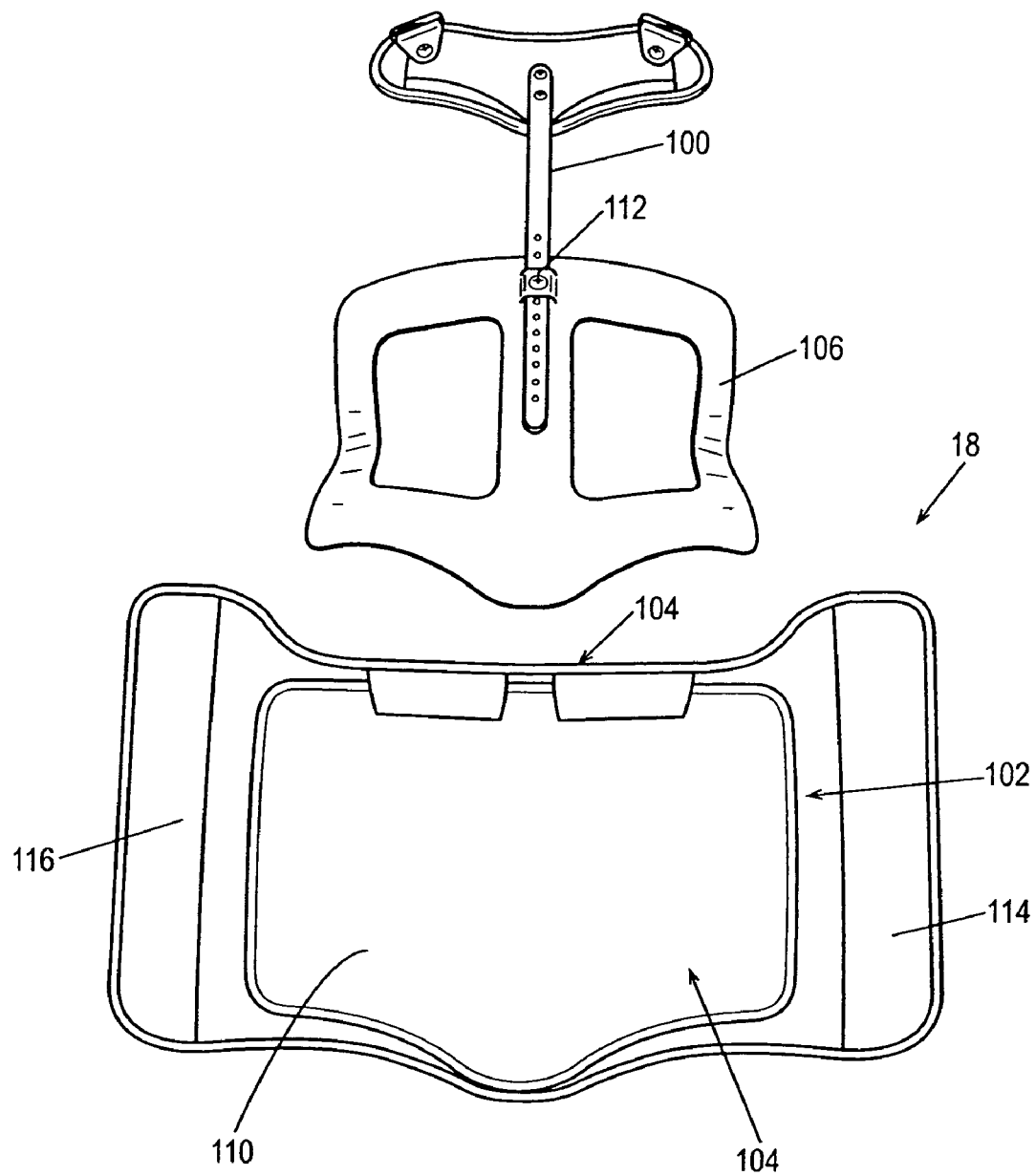
FIGS. 9–11 show an anterior support of the brace of FIG. 1, with the anterior support further including a sternal extension member.
Figure 10:
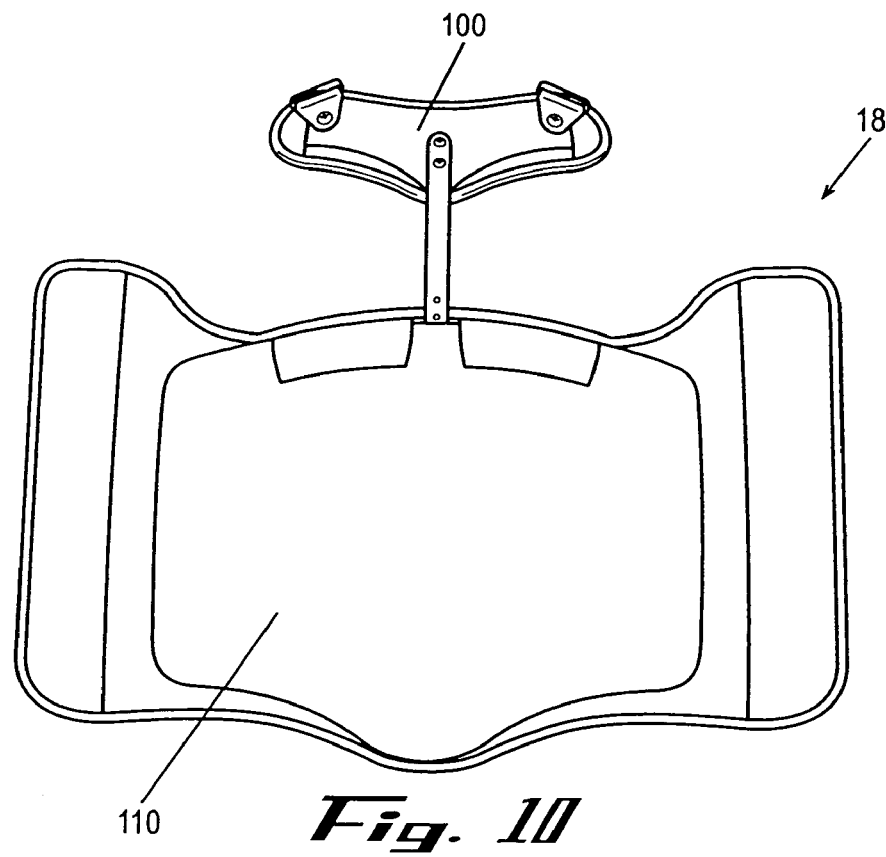
Figure 11:
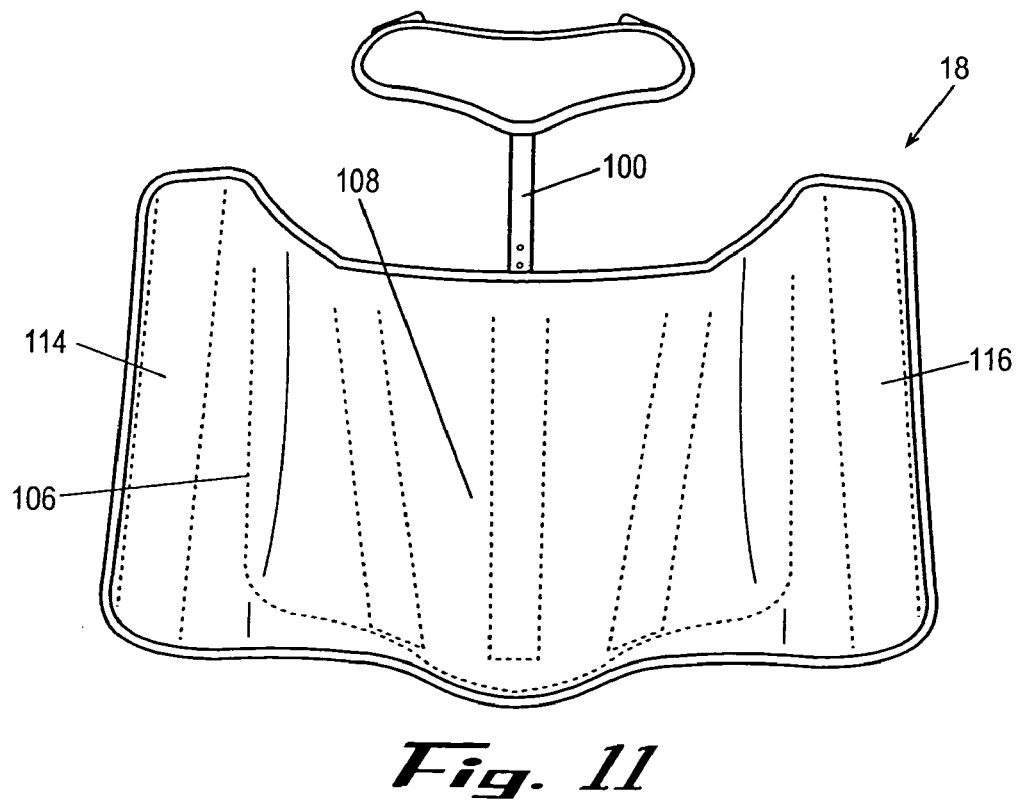
Figure 14:
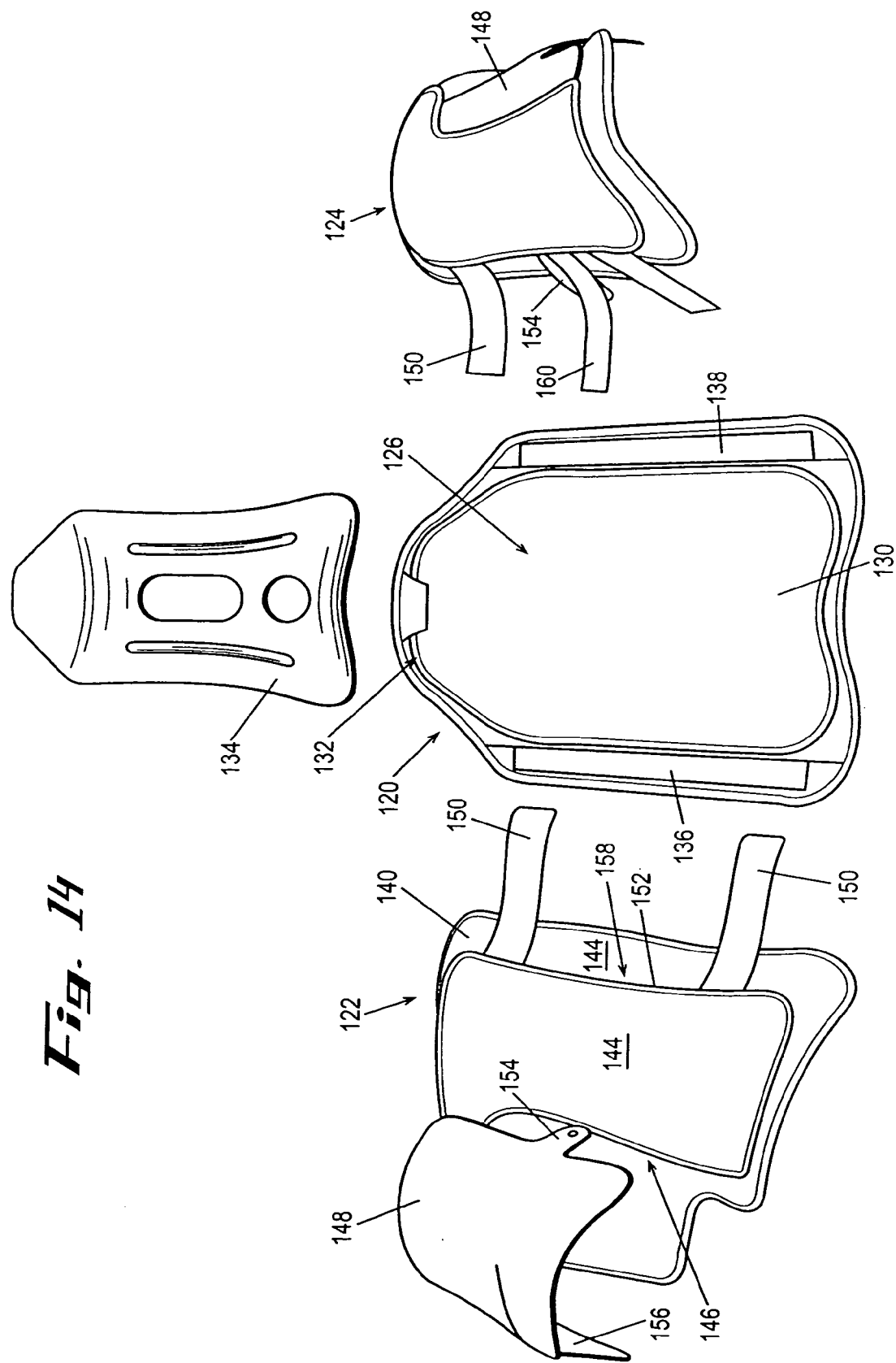
FIG. 14 is an exploded view of alternate embodiments of a posterior support and overlap supports.
Figure 15:
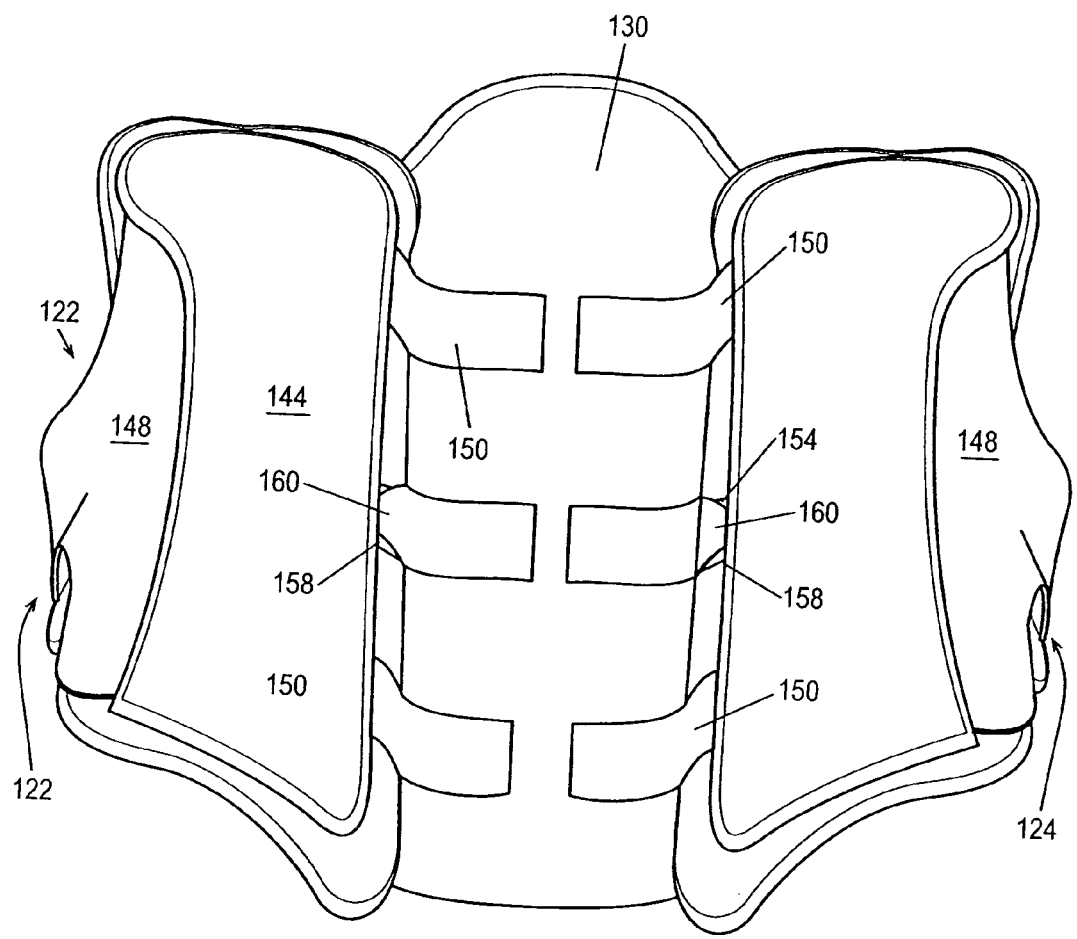
FIG. 15 is an exterior plan view of the supports of FIG. 14 assembled for use.
Figure 16:
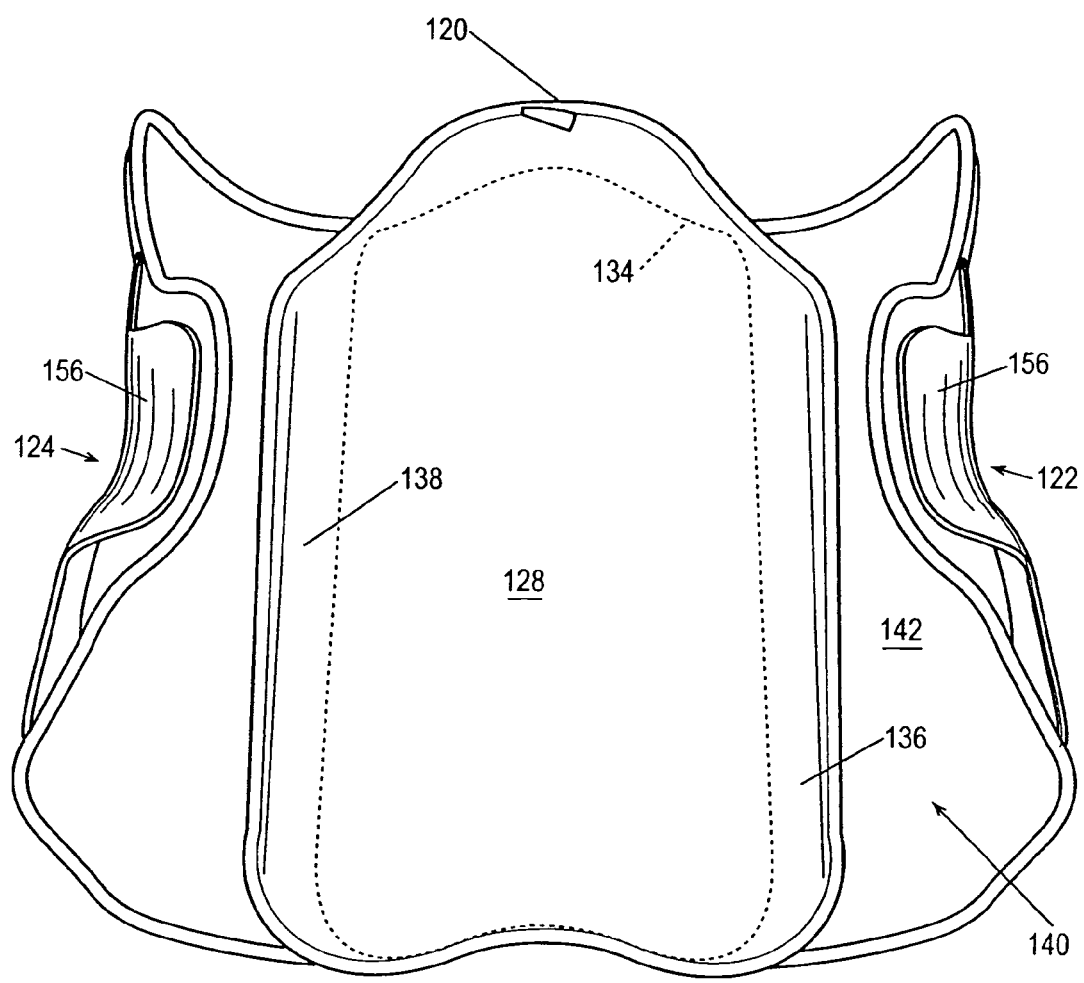
FIG. 16 is an interior plan view of the supports of FIG. 14 assembled for use.

FIGS. 9–11 show the anterior support 18 of the brace of FIG. 1, with the anterior support 18 further including a sternal extension member 100. The anterior support 18 includes a foam body 102 having a pocket 104 for receiving a rigid splint 106. The body 102 is preferably formed of a soft breathable material laminated to a foam and having an inner surface 108 (FIG. 11) and an opposite outer surface 110 provided by a flexible loop material suitable for releasably engaging a flexible hook material. The extension member 100 is preferably releasably mountable to the splint 106 as by use of screw 112 or other fasteners. The body 102 also preferably includes opposite side extensions 114 and 116 which extend from the side edges thereof. The extensions 114 and 116 are preferably made of the same material as the body 102 and include internal rigid stays running substantially the length of the extensions. In this regard, the term "extensions" will be understood to refer to portions of the body that extend substantially beyond the portion of the body that encases the rigid splint.

FIG. 12 shows installation of the brace 10 of FIG. 1 onto a user. In this regard, the brace 10 is first assembled as by installing the strap assemblies 14 and 16 and the supports 20 and 22 onto the posterior support 12, such as seen in FIGS. 6 and 7. Next, one of the strap assemblies, such as strap assembly 14 is secured to the anterior support 18. The brace 10 is then placed on the user as seen in FIG. 12, with the supports 20 and 22 underlying the anterior support 18, and the remaining strap assembly attached to the posterior support 12. The positions and/or tensions of the strap assemblies may then be adjusted to provide the desired fit.

As previously noted, and with reference to FIG. 13, the supports 20 and 22 are preferably installed on the posterior support 12 so that the supports 20 and 22, which are themselves substantially rigid, overlap at least a portion of the rigid splint 28 within the support 12. Additionally, when the brace 10 is installed, the supports 20 and 22 preferably extend beyond the edges of the rigid splint 106 within the anterior support 18 so as to at least partially overlap the rigid splint 106. This advantageously provides a modular spinal brace system incorporating four rigid plastic shells configured in an overlapping relationship. The overlapping relationship of the rigid splints coupled with the stabilizing function of the strap assemblies enhances lateral support of the brace. The brace further offers improved comfort and is convenient to use. As will be understood, the term "overlap" as used herein refers generally to the common orientation and is independent of whether each overlap support is positioned interior or exterior to the posterior or anterior support. Likewise, it will be understood that the overlap supports 20 and 22 may be initially attached to the anterior support 18 instead of the posterior support 12.

FIGS. 14–17.

With reference now to FIGS. 14–17, there are shown a posterior support 120 and overlap supports 122 and 124 in accordance with an alternate embodiment of the invention.

The posterior support 120 and the overlap supports 122 and 124 are configured for use with the anterior support 18, the strap assemblies 14 and 16, and the thoracic support 70 described above to provide a thoracic-lumbar-sacral orthosis.

The posterior support 120 is substantially identical to the posterior support 12 and preferably made of the same materials, except that it does not include the strips 32 and the slits 44. In this regard, the posterior support 120 preferably includes a foam body 126 having inner surface 128 and outer surface 130, and including a pocket 132 for receiving a rigid splint 134. Side extensions 136 and 138 preferably extend from the body 126 in the manner of the extensions 40 and 42 described above. The strap assemblies 14 and 16 attach to the posterior support 120 and the anterior support 18 in the same manner as described previously.

The overlap support 122 includes a foam body 140 having an inner surface 142 and an outer surface 144. A pocket 146 is defined adjacent the outer surface 144 and configured for receiving a rigid shell 148. A pair of strips 150 of hook material extend from a rear edge 152 of the pocket 146 for attachment of the body 140 to loop material of the outer surface 130 of the posterior support 120. The overlap support 124 is preferably substantially identical to the support 122, except it is configured for use on the opposite side.

The shells 148 for use in the supports 122 and 124 are preferably molded of a polymeric material and curved or otherwise anatomically shaped to conform to the general curves of a patient's sides The overlap supports 122 and 124 may be heated if desired, as by a heat gun, to soften them so that they may be custom fit to the patient. In configuring or custom-fitting the overlap supports 122 and 124, it is desired that the supports be shaped so as to wrap around the iliac crests of the patient and over the anterior superior iliac spines of the patient.

The shells 148 are further configured so that a portion of each shell 148 overlaps at least a portion of the rigid splint 134 of the posterior support 120 and at least a portion of the rigid splint 106 of the anterior support 18 when the overlap supports 122 and 124 are assembled with the posterior and anterior supports 120 and 18, respectively, to provide a brace.

Figure 17:
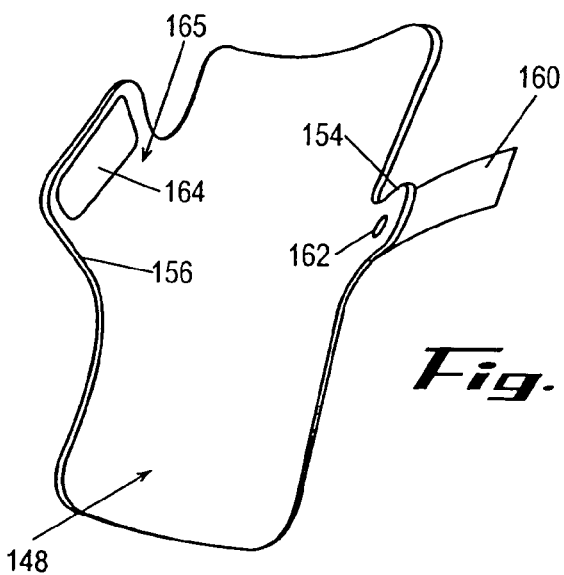
FIG. 17 is a close-up view of one of the overlap supports of FIG. 14.
Figure 18:
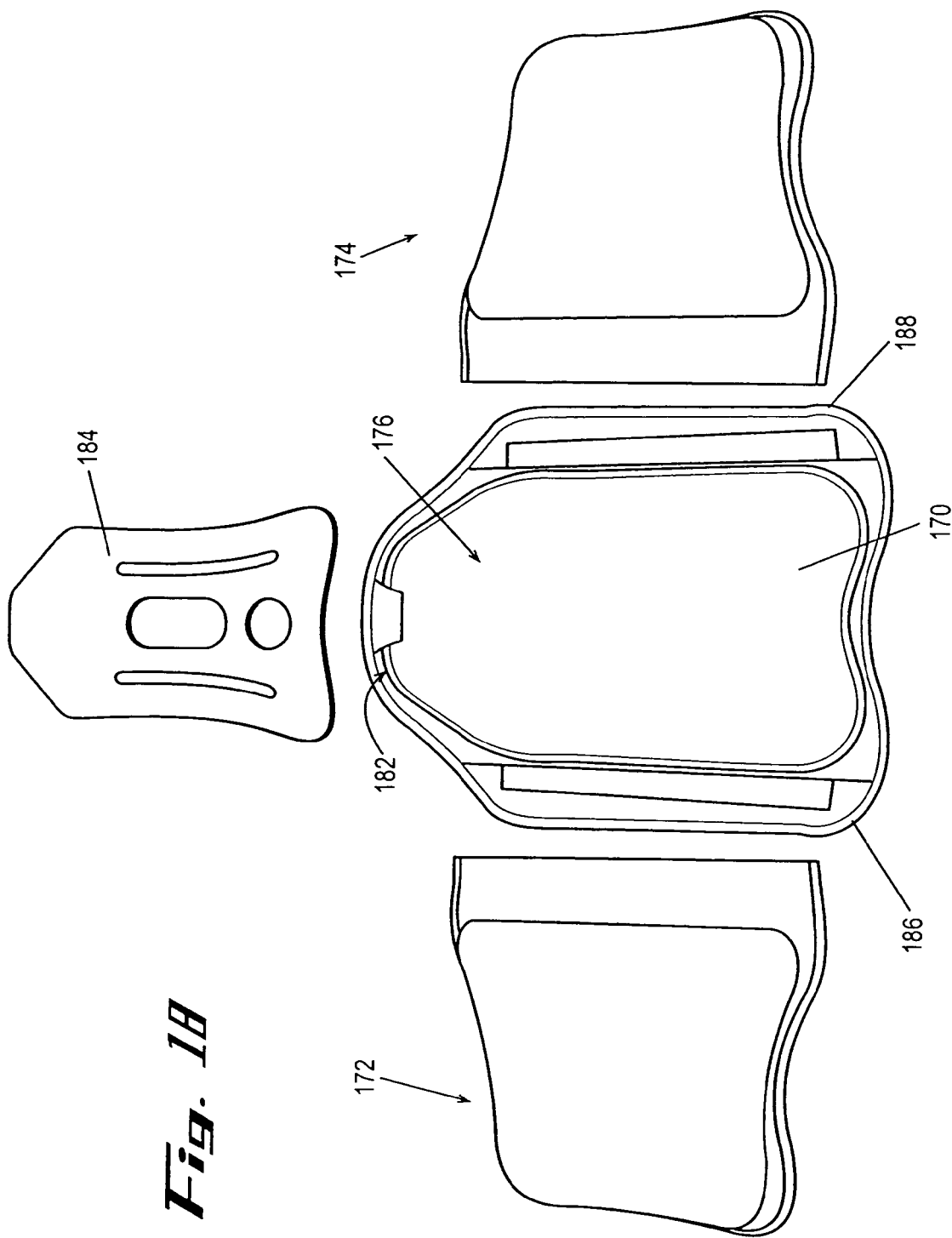
FIG. 18 is an exploded view of further alternate embodiments of a posterior support and overlap supports.

In this regard, and with particular reference to FIG. 17, each shell 148 preferably includes a rear extension 154 positionable to overly a portion of the rigid splint 134 of the posterior support 120 and a front extension 156 positionable to overly a portion of the rigid splint 106 of the anterior support 18 of an assembled brace. The extension 154 preferably extends through an opening 158 in the pocket 146 and includes a strip 160 of hook material secured thereto as by a fastener 162 for engaging the loop material of the outer surface 130 of the posterior support 120 in the manner of the strips 150. A strip of hook material 164 is preferably secured as by adhesive to the interior surface 165 of the extension 156 to assist in securing the shell 148 to the foam body 140.

FIGS. 18–21.

With reference now to FIGS. 18–21, there are shown aposterior support 170 and overlap supports 172 and 174 in accordance with another alternate embodiment of the invention. The posterior support 170 and the overlap supports 172 and 174 are configured for use with the anterior support 18, the strap assemblies 14 and 16, and the thoracic support 70 to provide a thoracic-lumbar-sacral orthosis.

The posterior support 170 is preferably substantially identical to the posterior support 120 and includes a foam body 176 having inner surface 178 and outer surface 180 of a loop material, a pocket 182 for receiving a rigid splint 184, and side extensions 186 and 188 extending from the body 176.

Figure 19:
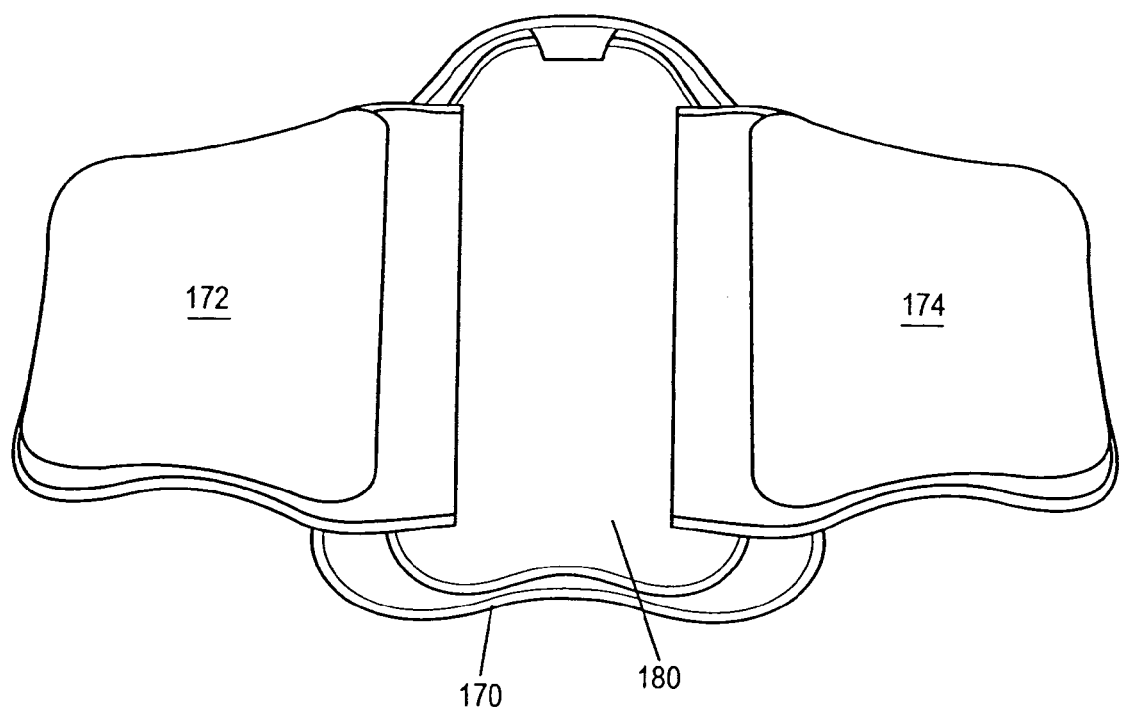
FIG. 19 is an exterior plan view of the supports of FIG. 18 assembled for use.

The overlaps supports 172 and 174 may be identical to one another and each preferably includes a foam body 190 having an internal stay 192. The stay 192 is preferably a thin piece of polyethylene bifurcated into a pair of fingers 194 and 196 extending from a base 198 to enable the stay 192 to better conform to the side of the user when a brace incorporating the supports 172 and 174 is worn by a user. As will be noted, the stay 192 is substantially rigid, yet is generally conformable to the shape of the user. It will be understood that the stay 192 may be rigid and preferably curved to conform generally to the shape of the user. A strip of hook material 200 is preferably attached to edge 202 of the body 190 for enabling releasable attachment the body 190 to the loop material of the surface 180 of the posterior support 170, such as seen in FIG. 19.

Figure 20:
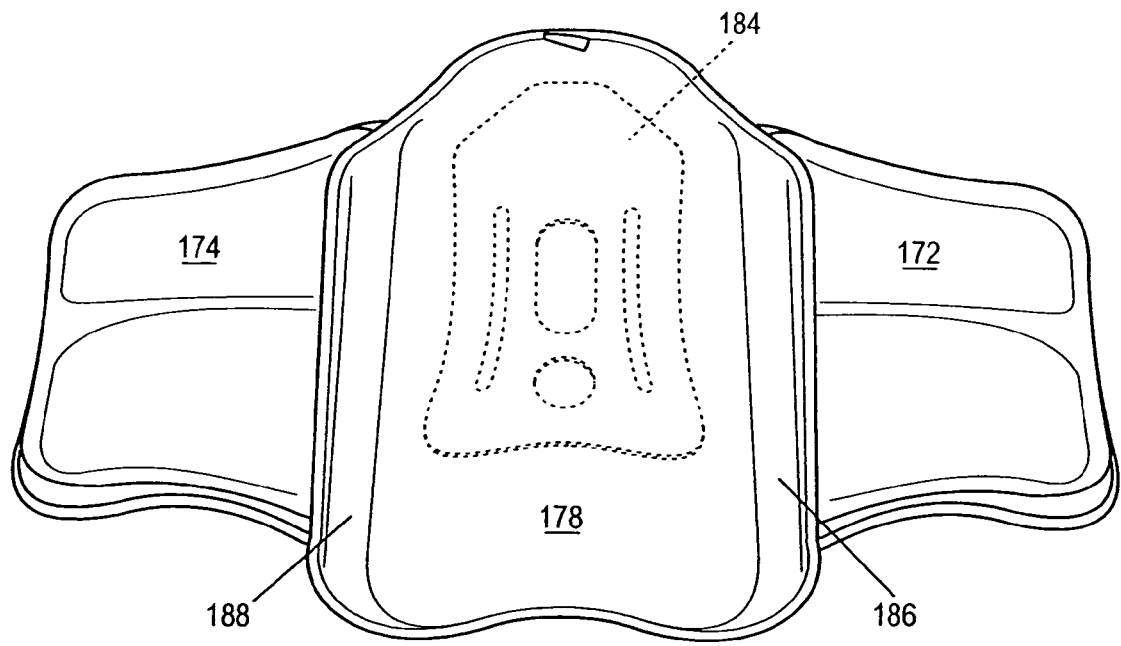
FIG. 20 is an interior plan view of the supports of FIG. 18 assembled for use.
Figure 21:
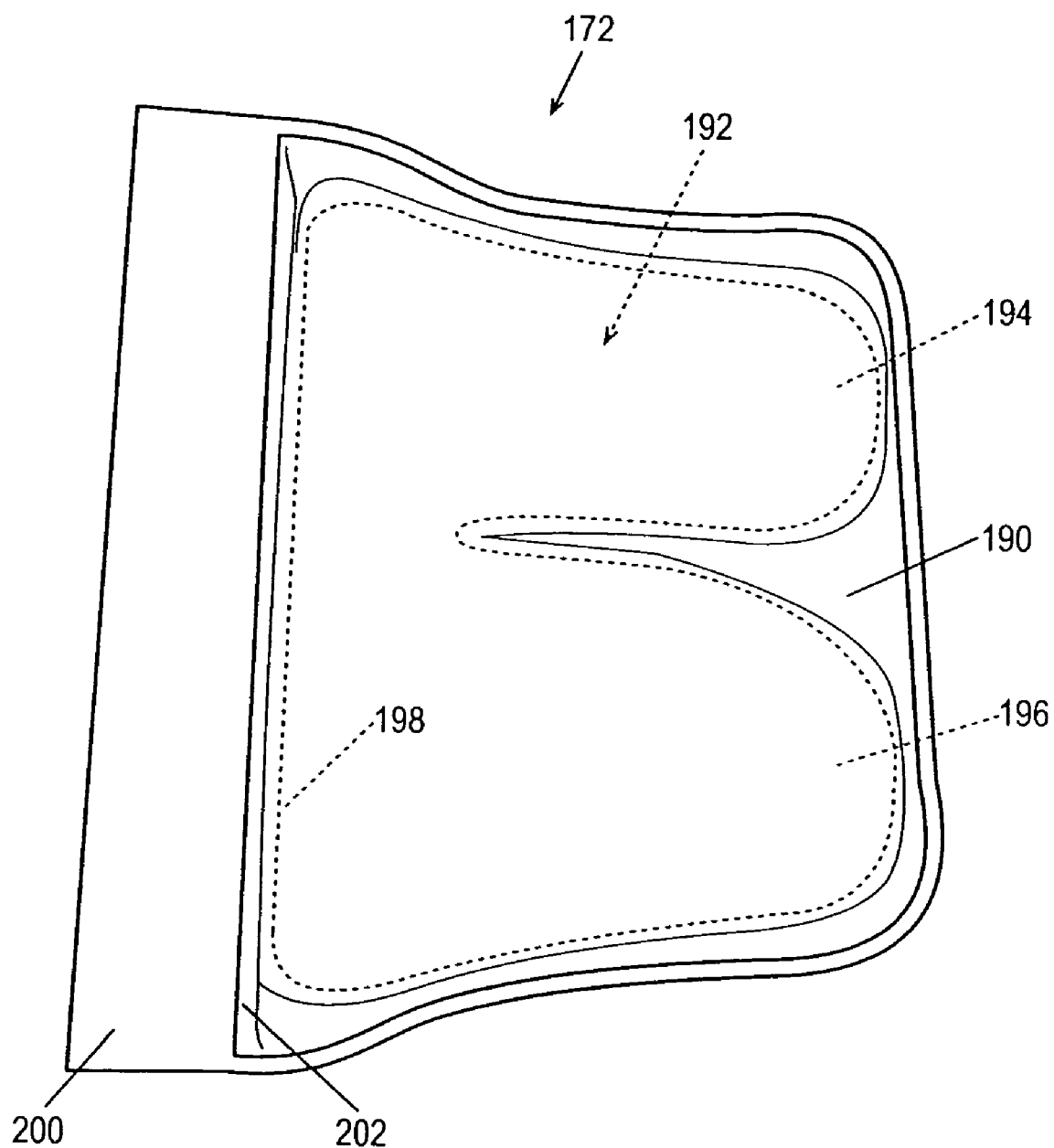
FIG. 21 is an interior plan view of one of the overlap supports of FIG. 18.

The overlap supports 172 and 174 are preferably installed on the posterior support 170 such that at least a portion of the base 198 of the stay 192 of each of the overlap supports 172 and 174 overlaps at least a portion of the splint 184 within the posterior support 170 (FIG. 20). Likewise, the fingers 194 and 196 of each overlap support 172 and 174 is positionable to overly at least a portion of the rigid splint 106 of the anterior support 18 of an assembled brace. The overlap supports 172 and 174 are preferably positioned so as to wrap around the iliac crests of the patient and over the anterior superior iliac spines of the patient.

FIG. 22.

Figure 22C:
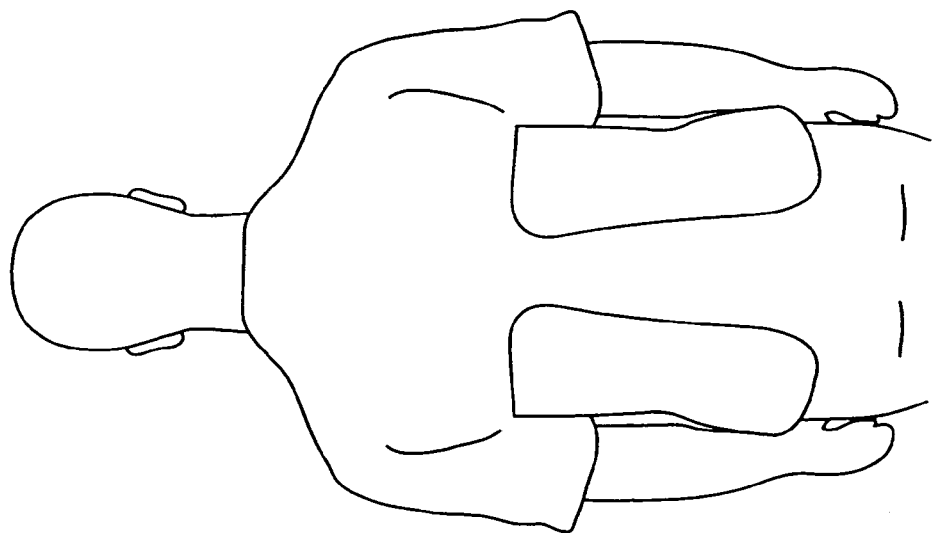
FIGS. 22A–22C illustrate preferred positioning of overlap supports so that they are wrapped around the iliac crests and over the anterior superior iliac spines of a user.
Figure 22B:
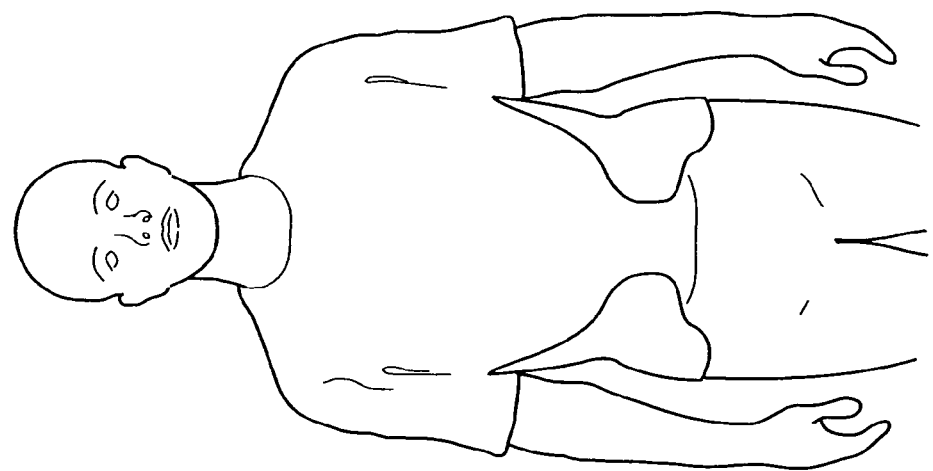
Figure 22A:
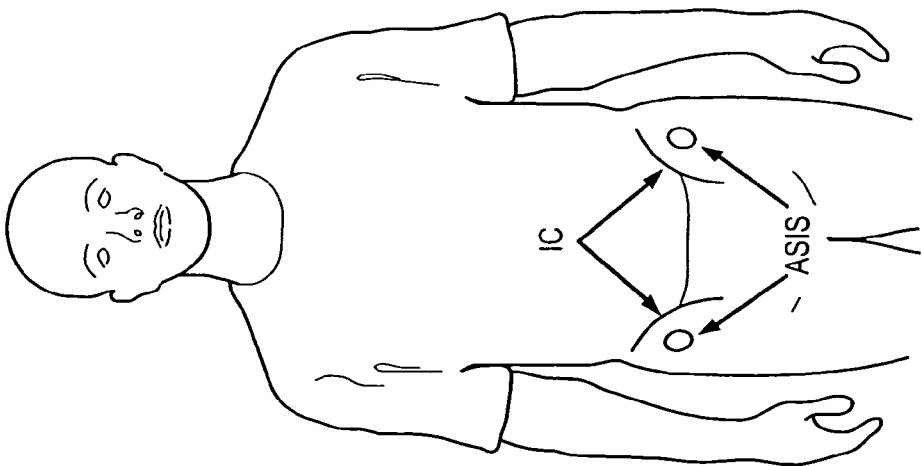

As noted in each of the foregoing embodiments, the overlap supports, e.g., the overlap supports 20 and 22, 122 and 124, 172 and 174, may be positioned so as to wrap around the iliac crests of the patient and over the anterior superior iliac spines of the patient. This is advantageous to prevent rotation. As will be appreciated, the anterior and posterior supports, such as the supports 12 and 18, and 120, serve to sandwich the pelvis of the user. This combination of the overlap supports preventing pelvic rotation and the anterior and posterior supports sandwiching the pelvis, has been observed to advantageously control pelvic tilt while maintaining the desired amount of flexion or extension of the spine. For the purpose of illustration, FIG. 22A shows the iliac crests (IC) and the anterior superior iliac spines (ASIS) of a user. FIG. 22B is a front view and FIG. 22C is a rear view showing the preferred positioning of the overlap supports, such as supports 20 and 22, to wrap around the IC and the ASIS.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A spinal orthosis for treating a spine, comprising:
   a posterior support having a substantially rigid posterior splint;
   an anterior support having a substantially rigid anterior splint;
   first and second overlapping supports releasably attachable to the posterior support, each overlapping support being a laminate made of a plurality of layers bonded together and comprising a layer of a flexible foam material, a layer of a rigid plastic strip, and a layer of a rigid plastic sheet material sandwiched between a pair of soft flexible sheet materials and molded together to yield a unitary and substantially rigid laminate material shaped to substantially conform to a side portion of a patient, wherein the first overlapping support is positionable relative to the posterior and the anterior supports when the orthosis is installed on a user so that a portion of the first overlapping support overlaps at least a portion of the posterior splint and the anterior splint, and the second overlapping support is positionable relative to the posterior and the anterior supports when the orthosis is installed on a user so that a portion of the second overlapping support overlaps at least a portion of the posterior splint and at least a portion of the anterior splint; and one or more straps attachable to the posterior support and the anterior support for securing the spinal orthosis on a patient.

2. The orthosis of claim 1, wherein the posterior support comprises a flexible material defining a pocket for receiving the posterior splint, with the flexible material including a plurality of strips of a hook material for releasably engaging loop material associated with the first and second overlapping supports for releasably attaching the first and second overlapping supports to the posterior support.

3. The orthosis of claim 1, wherein the anterior support comprises a flexible material defining a pocket for receiving the anterior splint.

4. The orthosis of claim 1, wherein the first and second overlapping supports are configured to be positionable to wrap around iliac crests portions and over anterior superior iliac spine portions of a patient.

5. The orthosis of claim 4, wherein the anterior and posterior supports are positionable to sandwich a pelvis portion of the patient, such that the orthosis inhibits tilting of the pelvis while maintaining a desired amount of flexion or extension of the spine.

* * * * *